United States Patent

Teng et al.

[11] Patent Number: 5,616,712
[45] Date of Patent: Apr. 1, 1997

[54] ACETYLENES DISUBSTITUTED WITH A PHENYL OR HETEROARYL GROUP AND A 2-THIO-1,2,3,4-TETRAHDROQUINOLINYL, 2-ALKYLTHIO-3,4-DIHYDROQUINOLINYL OR 2-ALKOXY-3,4-DIHYDROQUINOLINYL GROUP HAVING RETINOID-LIKE BIOLOGICAL ACTIVITY

[75] Inventors: Min Teng, Aliso Viejo; Richard L. Beard, Newport Beach; Diana Colon; Tien T. Duong, both of Irvine; Roshantha A. Chandraratna, Mission Viejo, all of Calif.

[73] Assignee: Allergan, Waco, Tex.

[21] Appl. No.: 442,223

[22] Filed: May 16, 1995

[51] Int. Cl.$^6$ .................. C07D 215/36; C07D 215/227; A61K 31/47
[52] U.S. Cl. .................................................. 546/158
[58] Field of Search ........................... 546/158; 514/311, 514/312

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 548/237 |
| 4,391,731 | 7/1983 | Boller | 252/299.62 |
| 4,695,649 | 9/1987 | Magami | 560/86 |
| 4,723,028 | 2/1988 | Shudo | 560/8 |
| 4,739,098 | 4/1988 | Chandraratna | 560/8 |
| 4,740,519 | 4/1988 | Shroot | 514/443 |
| 4,792,561 | 12/1988 | Walker | 514/312 |
| 4,810,804 | 3/1989 | Chandraratna | 514/311 |
| 4,826,969 | 5/1989 | Maignan | 536/55.2 |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 170105A | 2/1986 | European Pat. Off. . |
| 0176033 | 4/1986 | European Pat. Off. . |
| 0176032 | 4/1986 | European Pat. Off. . |
| 176034A | 4/1986 | European Pat. Off. . |
| 0253302 | 1/1988 | European Pat. Off. . |
| 0272921 | 6/1988 | European Pat. Off. . |
| 0284288 | 9/1988 | European Pat. Off. . |
| 0303915 | 2/1989 | European Pat. Off. . |
| 0315071 | 5/1989 | European Pat. Off. . |
| 0350846 | 7/1989 | European Pat. Off. . |

(List continued on next page.)

OTHER PUBLICATIONS

Martinez, *J. Med. Chem.*, vol. 35, pp. 620–628, 1992. 1992.
Olson, "A Dopamine Receptor . . . ", American Chemical Society, vol. 24, No. 9, pp. 1026–1031, 1981.
Zouboulis, "Effects of 13–Cis–. . . ", The Journal of Investigative Dermatology, vol. 96, No. 5, pp. 792–979, 1991.
Ridden, "Organ Maintenance . . . ", Journual of Cell Science, vol. 95, pp. 125–136, 1990.
Bahner, "Di– and Tri–methoxystyryl . . . ", Arzneim–Forsch./Drug Res., vol. 31(I), No. 3, pp. 404–406, 1981.
A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 pp. 358–360.
Conversion of Methyl Ketones into Terminal Acetylenes and (E)–Tri–substituted Olefins of Terpenoid Origin by Ei–ichi, Anthony O. King, and William L. Klima, *J. Org. Chem.* 45 No. 12, 1980 pp. 2526–2528.

*Primary Examiner*—C. Warren Ivy
*Assistant Examiner*—D. Margaret M. Mach
*Attorney, Agent, or Firm*—Gabor L. Szekeres; Robert J. Baran; Martin A. Voet

[57] ABSTRACT

Compounds of the formula

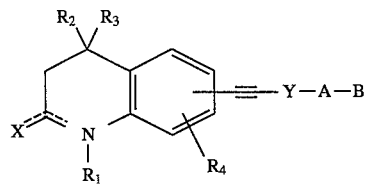

where the symbols are defined as in the specification.

19 Claims, No Drawings

U.S. PATENT DOCUMENTS

| | | | |
|---|---|---|---|
| 4,826,984 | 5/1989 | Berlin | 546/134 |
| 4,855,320 | 8/1989 | Chatterjee | 514/473 |
| 4,895,868 | 1/1990 | Chandraratna | 514/432 |
| 4,921,862 | 5/1990 | Walker | 514/312 |
| 4,927,948 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,840 | 6/1994 | Chandraratna | 546/318 |
| 5,324,844 | 6/1994 | Chandraratna | 514/456 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1993 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,567 | 3/1995 | Chandraratna | 514/252 |
| 5,399,586 | 3/1995 | Davies | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna | 514/337 |
| 5,434,173 | 7/1995 | Chandraratna | 514/354 |

FOREIGN PATENT DOCUMENTS

| | | |
|---|---|---|
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2190378 | 11/1987 | United Kingdom . |
| 8500806 | 2/1985 | WIPO . |
| 8504652 | 10/1985 | WIPO . |
| 9116051 | 10/1991 | WIPO . |
| 9203948 | 4/1992 | WIPO . |

OTHER PUBLICATIONS

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980, pp. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'-Diacyl-1,1'-biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3-g]isoquinoline Antipsychotics, Gary L. Olson, et al. *American Chemical Society*, 1981, Vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem*, 387, (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., *Journal of Cell Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar. 1991. pp. 341–348.

Synthesis and Evaluation of Stilbene and Dihydrostilbene Derivatives as Potential Anticancer Agents That Inhibit Tubulin Polymerization by Cushman, Mark et.al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No.4, pp. 211–214, 1991.

Di–and Tri–methoxystyryl Derivatives of Heterocyclic Nitrogen Compounds by Bahner, C.T. et al. Arzneim–Forsch./Drug Res, 31 (I), Nr. 3 (1981), pp. 404–406.

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

ACETYLENES DISUBSTITUTED WITH A PHENYL OR HETEROARYL GROUP AND A 2-THIO-1,2,3,4-TETRAHDROQUINOLINYL, 2-ALKYLTHIO-3,4-DIHYDROQUINOLINYL OR 2-ALKOXY-3,4-DIHYDROQUINOLINYL GROUP HAVING RETINOID-LIKE BIOLOGICAL ACTIVITY

BACKGROUND OF THE INVENTION

1. Field of the Invention

The present invention is directed to novel compounds which have retinoid-like biological activity. More specifically, the present invention relates to ethyne compounds which have a phenyl or a heteroaryl substituent and also a 2-thio-1,2,3,4-tetrahydroquinolinyl, 2-alkylthio-1,2,3,4-tetrahydroquinolinyl or 2-alkoxy-1, 2,3,4-tetrahydroquinolinyl substituent. The phenyl or heteroaryl group may have an acid or ester function, which may also be converted to an alcohol, aldehyde or ketone, or derivatives thereof, or may be reduced to —$CH_3$.

3. Related Art

Compounds which have retinoid like activity are well known in the art, and are described in numerous United States and foreign patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. No. 4,810,804 discloses such disubstituted acetylene compounds wherein one of the substituents of the acetylene group is a substituted phenyl group, and the second substituent is substituted or unsubstituted 6-chromanyl, 6-thiochromanyl or 6-tetrahydroquinolinyl group. The compounds disclosed and claimed in U.S. Pat. No. 4,810,804 have retinoid acid-like biological activity.

A published European patent application of the present applicant (Publication No. 0284288, published on Sep. 28, 1988) describes compounds having retinoic acid-like activity which are 4,4-disubstituted 6-chromanyl, 4,4-disubstituted 6-thiochromanyl and 4,4-disubstituted 6-tetrahydroquinolinyl acetylenes also substituted by a substituted heteroaryl group.

U.S. Pat. Nos. 5,013,744, 5,023,341, 5,053,523, and 5,089,509 describe ethyne compounds substituted with a heteroaromatic or monocyclic aromatic substituent and also with a second monocyclic aromatic or heteroaromatic substituent. U.S. Pat. No. 5,399,561 describes ethyne compounds which have a phenyl or a heteroaryl substituent and also a 2-oxochromanyl, 2-oxothiochromanyl or 2-oxo-1,2,3,4-tetrahydroquinolinyl substituent. The compounds described in these patents have retinoid-like biological activity. Numerous further United States patents and applications for patent assigned to the same assignee as the present invention, are directed to compounds having retinoid-like biological activity.

SUMMARY OF INVENTION

The present invention relates to compounds of Formula 1

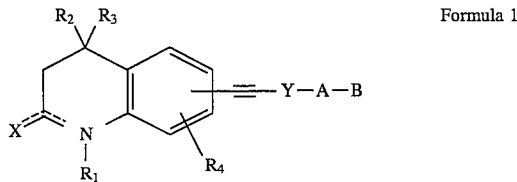

Formula 1 where the dotted lines represent a bond or the absence of a bond;

$R_1$ is H, lower alkyl of 1 to 10 carbons, lower alkenyl of 2 to 10 carbons, phenyl $C_1$–$C_6$ lower alkyl, phenyl $C_2$–$C_6$ lower alkenyl, heteroaryl $C_1$–$C_6$ lower alkyl, heteroaryl $C_2$–$C_6$ lower alkenyl, or $R_1$ is absent;

X is S or O, $R_5$S or $R_5$O where $R_5$ is lower alkyl of 1 to 10 carbons, lower alkenyl of 2 to 10 carbons, phenyl $C_1$–$C_6$ lower alkyl, phenyl $C_2$–$C_6$ lower alkenyl, heteroaryl $C_1$–$C_6$ lower alkyl, heteroaryl $C_2$–$C_6$ lower alkenyl, with the proviso that when $R_1$ is H then X is S;

$R_2$ and $R_3$ are hydrogen, lower alkyl of 1–6 carbons, or halogen;

$R_4$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

Y is phenyl or a heteroaryl group selected from a group consisting of pyridyl, thienyl, furyl, pyridazinyl, pyrimidinyl, pyrazinyl, thiazolyl, imidazoly and oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical composition comprising a compound of Formula 1 in admixture with a pharmaceutically acceptable excipient.

In another aspect, this invention relates to the process for making a compound of Formula 1, which process comprises:

reacting a compound of Formula 2 with an alkylating or alkenylating agent of the formula $R_5$—Z (Z is a leaving group, such as I) to obtain a compound of Formula 1 where $R_1$ is absent and X is $R_5O$; or reacting a compound of Formula 3 with a thiolating agent (such as Lawesson's reagent) to obtain a compound of Formula 1 where X is S; or reacting a compound of Formula 4 with an alkylating or alkenylating agent of the formula $R_5$—Z to obtain a compound of Formula 1 where $R_1$ is absent and X is $R_5S$. In Formulas 2, 3 and 4 the symbols are defined the same as in connection with Formula 1.

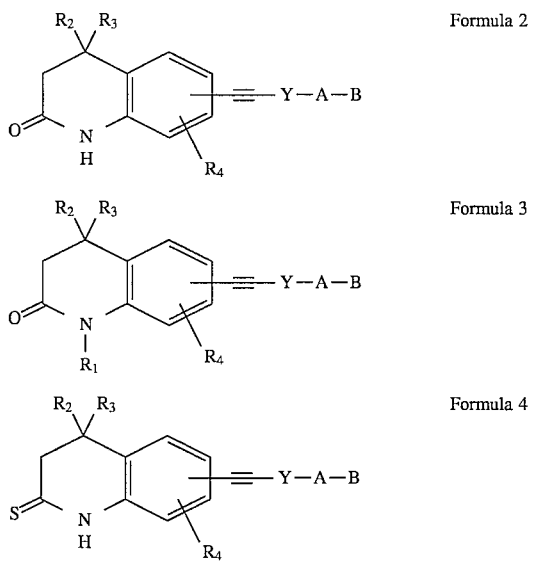

Formula 2

Formula 3

Formula 4

Still further the present invention relates to the processes of homologating a compound of Formula 1 where A is $(CH_2)_n$ and n is 0–4 to give an acid of Formula 1; or converting an acid of Formula 1 to a salt; or forming an acid addition salt;

converting an acid of Formula 1 to an ester; or converting an acid of Formula 1 to an amide; or reducing an acid of Formula 1 to an alcohol or aldehyde; or converting an alcohol of Formula 1 to an ether or ester; or oxidizing an alcohol of Formula 1 to an aldehyde; or converting an aldehyde of Formula 1 to an acetal; or converting a ketone of Formula 1 to a ketal.

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Unless stated otherwise in these specifications lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where $R_{11}$ is defined as above.

The term "amides" has the meaning classically accorded that term in organic chemistry. In this instance it includes the unsubstituted amides and all aliphatic and aromatic mono- and di- substituted amides.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention may contain one or more double bonds, and therefore may have trans and cis (E and Z) isomers. In adddition, the compounds of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference now to Formula 1, the preferred compounds of this invention are those where Y is phenyl, pyridyl, thienyl or furyl, with the phenyl derivatives being particularly preferred. When Y is phenyl, compounds are preferred where the ethynyl group and the A—B group are attached to the 1 and 4 positions respectively of a benzene ring (i.e., where the phenyl moiety of the compound is para substituted). When the Y group is pyridyl, thienyl or furyl, compounds are preferred where the ethynyl group and the A—B group are attached to the 2 and 5 positions respectively of a pyridine ring (the 6 and 3 positions of the nicotinic acid nomenclature being equivalent to the 2/5 designation in the pyridine nomenclature) or to the 5 and 2 positions respectively of a thiophene or furan group, respectively. Compounds where Y is phenyl, and where the phenyl group is para substituted in the above-described manner, are particularly preferred.

The ethynyl group is preferably attached to the 6 or to the 7 position of the quinoline nucleus.

With regard to the A—B side chain (substituent) on the phenyl or heteroaryl group Y, compounds are preferred where A is $(CH_2)_n$ and n is 0. With regard to group B, compounds are preferred where B is —COOH, an alkali metal salt or organic amine salt, or a lower alkyl ester thereof.

Regarding the substituents $R_2$ and $R_3$, compounds are preferred where these substituents are lower alkyl of 1 to 6 carbons, most preferably methyl.

The $R_4$ substituent is preferably H or lower alkyl of 1 to 6 carbons, even more preferably H or $CH_3$. Moreover, the $R_4$ group is preferably attached to the otherwise unoccupied 6 or 7 position of the quinoline nucleus.

Referring now to the $R_1$ group of the compounds of the invention in accordance with Formula 1, the preferred compounds are where $R_1$ is H, lower alkyl of 1 to 10 carbons, including branch chained lower alkyl, or benzyl.

When X is $R_5S$ or $R_5O$, then $R_5$ is preferably lower alkyl of 1 to 10 carbons, including branch chained lower alkyl.

The most preferred compounds of the invention are shown in Table 1 with reference to Formula 5 and Formula 6.

TABLE 1

| Compound # | Formula | position of ≡ on quinoline nucleus | X' | R'$_1$ | R'$_8$ |
|---|---|---|---|---|---|
| 5 | 5 | 6 | O | i-propyl | ethyl |
| 6 | 6 | 6 | O | i-propyl | ethyl |
| 7 | 5 | 6 | S | i-propyl | ethyl |
| 8 | 5 | 6 | S | H | ethyl |
| 9 | 6 | 6 | S | methyl | ethyl |
| 10 | 6 | 6 | S | n-heptyl | ethyl |
| 11 | 6 | 6 | O | i-propyl | H |
| 12 | 5 | 6 | S | i-propyl | H |
| 13 | 5 | 6 | S | H | H |
| 14 | 6 | 6 | S | methyl | H |
| 15 | 6 | 6 | S | n-heptyl | H |
| 22 | 5 | 7 | S | H | ethyl |
| 23 | 6 | 7 | S | methyl | ethyl |
| 28 | 6 | 7 | O | i-propyl | ethyl |
| 31 | 5 | 7 | O | i-propyl | ethyl |
| 32 | 5 | 7 | S | i-propyl | ethyl |
| 33 | 5 | 7 | S | H | H |
| 34 | 6 | 7 | S | methyl | H |
| 35 | 6 | 7 | O | i-propyl | H |
| 36 | 5 | 7 | S | i-propyl | H |
| 37 | 5 | 6 | O | benzyl | ethyl |
| 38 | 5 | 6 | O | n-heptyl | ethyl |
| 39 | 5 | 6 | O | benzyl | H |
| 40 | 5 | 6 | O | n-heptyl | H |

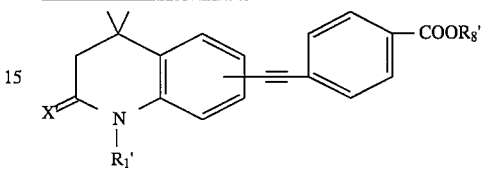

Formula 5

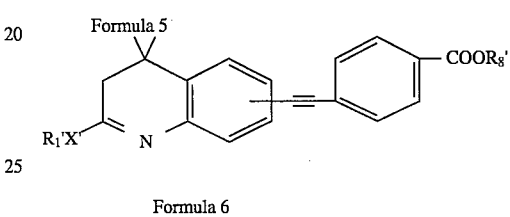

Formula 6

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases. in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The results of this assay for certain examplary compounds of the invention are shown in Table 2 below. $IC_{80}$ is that concentration of the test compound (expresed in nanomolar (nmol)) which results in 80 per cent inhibition of the ODC induction activity by TPA.

TABLE 2

| Compound # | $IC_{80}$ (nanomolar) |
|---|---|
| 5 | 6.4 |
| 6 | >100 |
| 7 | 5.5 |

TABLE 2-continued

| Compound # | $IC_{80}$ (nanomolar) |
|---|---|
| 8 | 54 |
| 9 | 29 |
| 10 | >60 |
| 22 | 6.0 |
| 31 | 2.9 |
| 32 | 0.2 |
| 38 | >100 |

SPECIFIC EMBODIMENT

Synthetic Processes for Preparing Compounds of the Invention

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and/or adjusted by those skilled in the art without departing from the scope and spirit of the invention.

Broadly speaking, compounds of the present invention are prepared from compounds of Formula 2, as this formula is defined above. Compounds of Formula 2 are 2-oxo-1,2,3,4-tetrahydroquinoline derivatives which are substituted in the 6 or 7 position with an arylethynyl or heteroarylethynyl group. Compounds of Formula 2 can be obtained in accordance with the teachings of U.S. Pat. No. 5,399,561 the specification of which is expressly incorporated herein by reference. Specifically, formula 42 in Column 17 of said reference patent discloses 6-aryl or 6-heteroaryl substituted 2-oxo-1,2,3,4-tetrahydroquinoline derivatives which are suitable as starting materials for synthesis of compounds of the present invention and which are encompassed by Formula 2 of the instant description. Formula 49 in Column 19 of said reference patent discloses 7-aryl or 7-heteroaryl substituted 2-oxo-1,2,3,4-tetrahydroquinoline derivatives which are suitable as starting materials for synthesis of compounds of the present invention and which are also encompassed by Formula 2 of the instant description.

Reaction Scheme 1

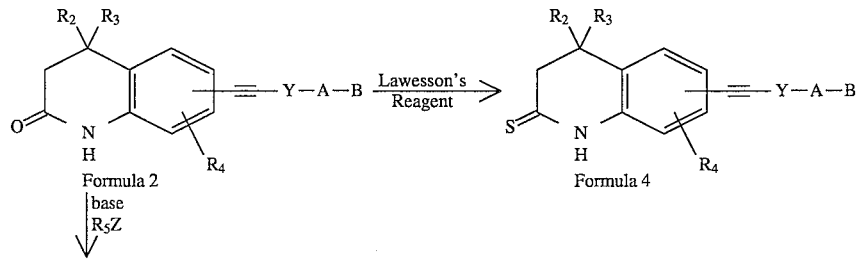

-continued
Reaction Scheme 1

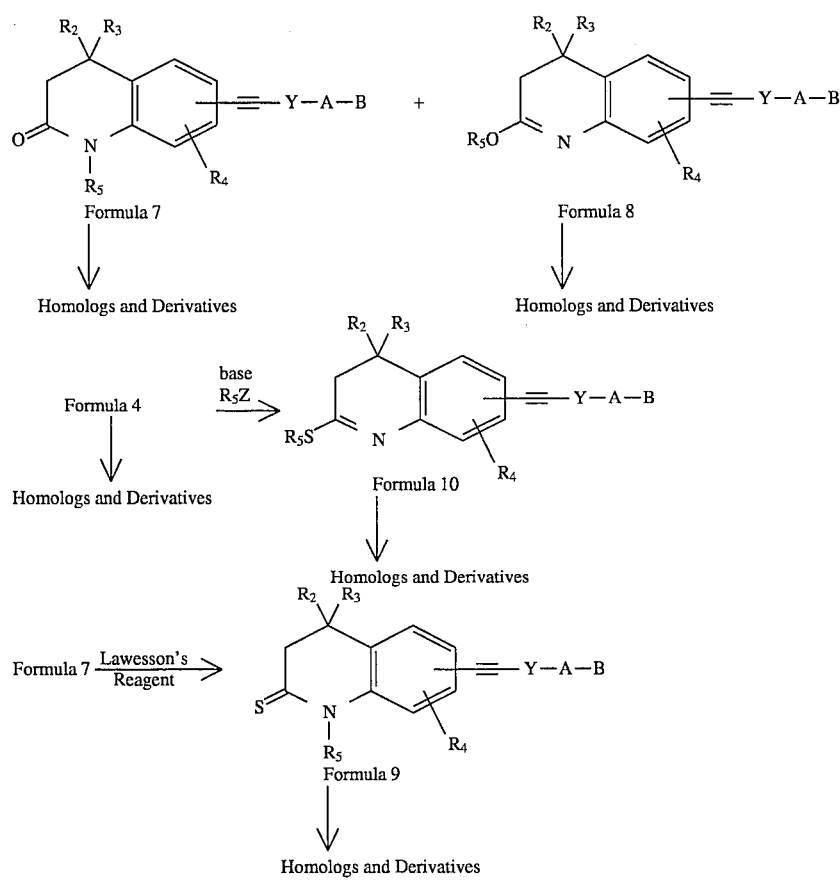

Referring now to Reaction Scheme 1 of the instant description, compounds of Formula 2 are treated with base and a reagent $R_5$—Z. The group $R_5$ of the reagent is defined as in connection with Formula 1, typically $R_5$ is an alkyl, alkenyl, aryl-alkyl or heteroaryl-alkyl group. Z is a leaving group which renders the $R_5$—Z reagent an "alkylating agent", Z is typically halogen, preferably bromine or iodine. Examples for the alkylating agent used for the preparation of the compounds of the present invention are methyl iodide, isopropyl iodide, n-heptyl iodide and benzyl bromide. The alkylation reaction is typically conducted in an aprotic polar solvent such as dimethylformamide in the presence of strong base, such as sodium hydride. The alkylation reaction typically provides a mixture of N-alkylated and O-alkylated products, that is compounds shown by Formula 7 and Formula 8 in the reaction scheme. These compounds can be separated from one another by conventional techniques, for example by chromatography. Compounds of Formula 7 are N-alkylated or alkenylated etc. derivatives. Compounds of Formula 8 are 2-O-alkylated or alkenylated etc. derivatives. Compounds of Formula 7 as well as compounds of Formula 8 can be converted into "homologs and derivatives" which are still within the scope of the present invention. Conversion to such "homologs and derivatives" may involve transformation of the A—B functionality, for example by saponification of an ester group, by formation of an amide or by homologation of an acid or ester. These and other related transformations are described below.

Referring still to Reaction Scheme 1, the 2-oxo function of the 1,2,3,4-tetrahydroquinoline moiety of the compounds of Formula 7 is converted to a thio group by a suitable "thiolating" reagent, typically and preferably with Lawesson's reagent. The latter reaction is typically conducted in a hydrocarbon solvent with moderate heating, preferably in benzene under refluxing conditions. The "thiolation" reaction provides compounds of Formula 9 wherein the $R_5$ is other than hydrogen. The compounds of Formula 2 can also be subjected to thiolation, preferably with Lawesson's reagent under conditions such as described above, to provide compounds of Formula 4 within the scope of the present invention. Compounds of Formula 4 are reacted with the "alkylating agent $R_5$—Z, typically in an inert ether-type solvent such as tetrahydrofuran, in the presence of strong base, such as sodium hydride, to provide the S-alkylated derivatives of Formula 10, within the scope of the present invention.

Reaction Scheme 2

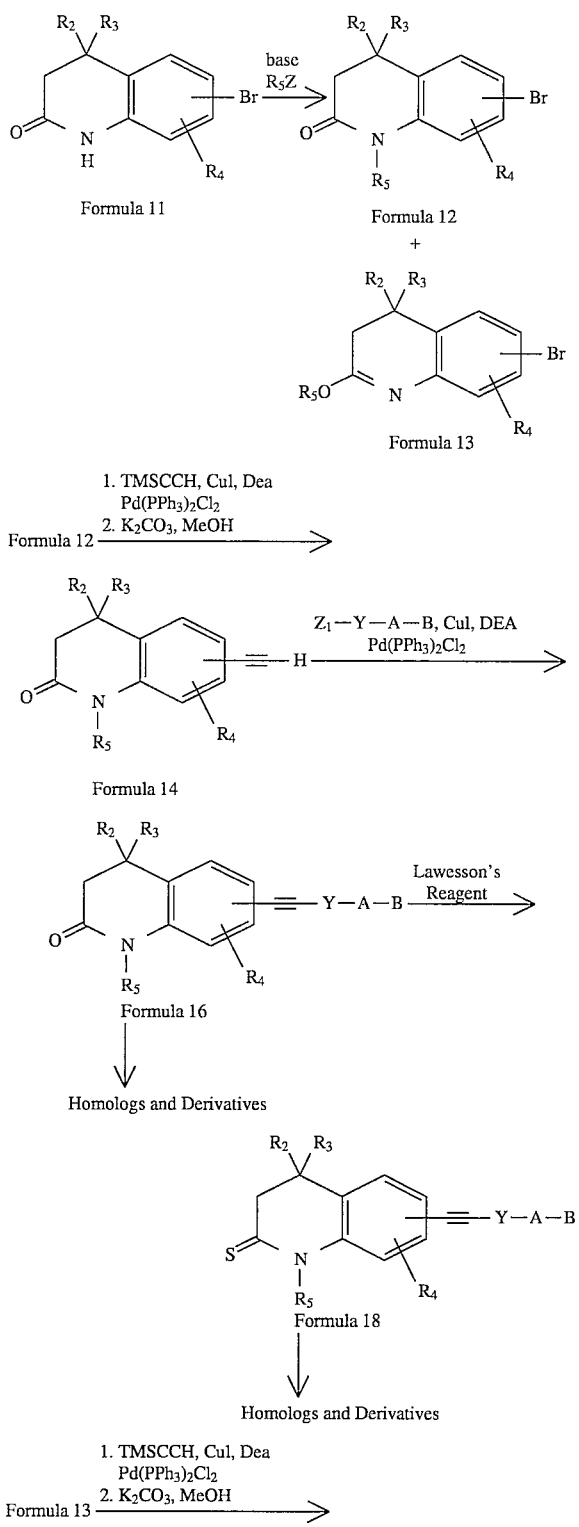

-continued
Reaction Scheme 2

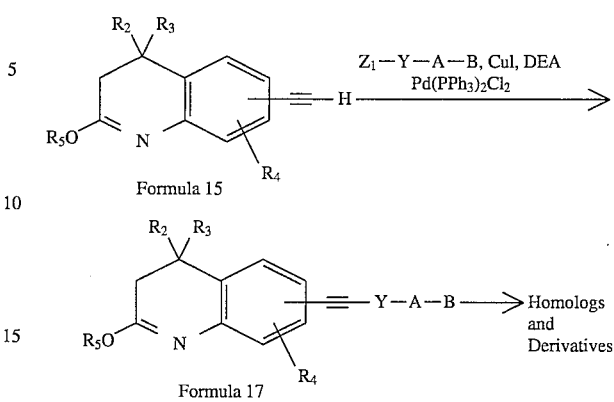

Referring now to Reaction Scheme 2, another synthetic scheme suitable for the synthesis of the compounds of the present invention is disclosed. In accordance with this scheme, a 6-bromo- or a 7-bromo-2-oxoquinoline derivative of Formula 11 is reacted with the alkylating agent $R_5$—Z to yield the corresponding N-alkylated derivative of Formula 12 plus the corresponding O-alkylated derivative of Formula 13. A specific example of the starting materials in accordance with Formula 11 of the instant description is 4,4-dimethyl-6-bromo-2-oxo-1,2,3,4-tetrahydroquinoline which is described in Column 24 of the referenced U.S. Pat. No. 5,399,561. Another specific example of the starting materials in accordance with Formula 11 of the instant description is 4,4-dimethyl-7-bromo-2-oxo-1,2,3,4-tetrahydroquinoline the preparation of which is described in the experimental section of the present specification. The N and O alkylated bromo compounds of Formula 12 and Formula 13 can be converted into the corresponding 6- or 7-ethynyl derivatives (Formulas 14 and 15 in Reaction Scheme 2), and thereafter into the corresponding 6- or 7-arylethynyl or 6- or 7-heteroarylethynyl derivatives (Formulas 16 and 17 in Reaction Scheme 2) substantially in accordance with the teaching of U.S. Pat. No. 5,399,561, and specifically as is shown in Columns 17 and 18 in Reaction Scheme 6 of that reference patent for the conversion of formula 38 to formula 42 in the reference. In summary, these transformations proceed through introduction of a (trimethylsily)acetylene group in place of the bromo function by coupling with (trimethylsilyl)acetylene in the presence of cuprous iodide and a suitable catalyst, typically having the formula $Pd(PQ_3)_2Cl_2$ (Q is phenyl). The reaction is typically conducted in the presence of a bis(triphenylphosphine) palladium (II) chloride catalyst and an acid acceptor (such as diethylamine or triethylamine) under an inert gas (argon) atmosphere, by allowing the reaction to proceed at room temperature or by heating in a sealed tube. Thereafter, the trimethylsilyl group is removed by treatment with base, such as potassium carbonate, and the resulting ethynyl compounds of Formula 14 and 15 are coupled with the reagent $Z_1$—Y—A—B where $Z_1$ is halogen. In other words, the phenyl or heteroaryl substitutent is attached to the 6- or 7-ethynyl-1,2,3,4-tetrahydroquinoline derivative by reacting the latter with a halogen substituted phenyl or heteroaromatic compound of the formula $Z_1$—Y—A—B, in which the phenyl or heteroaromatic nucleus (Y) either has the desired substituent [A—B] or wherein the actual subsituent A—B can be readily converted to the desired substituent by means of organic reactions well known in the art. The coupling reaction is affected directly in the presence of cuprous iodide, a suitable catalyst, typically of the formula Pd(PQ3)Cl$_2$ and an acid acceptor, such as triethylamine, at room temperature or by heating in a sealed tube under an inert gas (argon) atmosphere. Alternatively, a metal salt, such as the zinc salt derived from the ethynyl compounds of Formula 14 or 15 can be reacted with the reagent $Z_1$—Y—A—B in the presence of a palladium complex catalyst having the formula Pd(PQ$_3$)$_4$ (Q is phenyl) or similar complex.

The products of the latter coupling reactions are the N-alkylated 2-oxo-1,2,3,4-tetrahydroquinoline derivatives of Formula 16 and the O-alkoxylated-1,2,3,4-tetrahydroquinoline derivatives of Formula 17. Reaction of the compounds of Formula 16 with a thiolating reagent (Lawesson's reagent) produces the 2-thio derivatives of the present invention in accordance with Formula 18.

The compounds of the present invention shown by the formulas in Reaction Schemes 1 and 2 can be converted to further compounds within the scope of the invention by certain transformations which, per se, are known in the art. Similar synthetic transformations can be performed on the A—B functionality of the reagent $Z_1$—Y—A—B which is used in accordance with Reaction Scheme 2 for the preparation of the compounds of the invention. These transformations are briefly mentioned below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is (CH$_2$)$_n$ (n is 1–5) is to subject the compounds of Formula 1, where B is an acid or other function, to homologation, using the well known Arndt-Eistert method of homologation, or other known homologation procedures. Similar homologations (and several of the other herein mentioned synthetic transformations) can be transformed on the reagent $Z_1$—Y—A—B. Compounds of the invention, where A is an alkenyl group having one or more double bonds can be made, for example, by having the requisite number of double bonds incorporated into the $Z_1$—Y—A—B which is reacted with the ethyne compound or its metal salt, as is described in the reference U.S. Pat. No. 5,399,561 patent, or shown in Reaction Scheme 2. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of the invention where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropylamide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium or lithium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1977), or dimethyl sulfoxide/ oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

SPECIFIC EXAMPLES 4,4-Dimethyl-2-oxo-1,2,3,4-tetrahydro-6[(trimethylsilyl)ethynyl quinoline (Compound 2)

To a solution of 2.33 g (7.8 mmol) of 4,4-dimethyl-6-bromo-2-oxo-1,2,3,4-tetrahydroquinoline (Compound 1) in 40 ml of triethylamine which was degassed under argon for 15 min in a sealable tube, were added successively 0.368 g (1.96 mmol) of copper(I)iodide, 3.9 ml, (20.5 mmol) of (trimethylsilyl)acetylene, and 1.29 g (1.84 mmol) of bis-(triphenylphosphine)palladium(II) chloride. The reaction mixture was degassed for an additional 5 min. The tube was sealed and the reaction was heated at 50° C. for 72 h. Thereafter, the reaction mixture was concentrated in vacuo and the residue was purified by flash chromatography (silica, 10% ethyl acetate in hexane) to give the title compound as a white solid.

PNMR (CDCl$_3$) δ7.78 (1H, b), 7.41 (1H, d, J=1.7 Hz), 7.30 (1H, dd, J=8.2 Hz, 1.7 Hz), 6.67 (1H, d, J=8.2 Hz), 2.49 (2H, s), 1.33 (6H, s), 0.26 (9H, s).

4,4-Dimethyl-2-oxo-1,2,3,4-tetrahydro-6-ethynylquinoline (Compound 3)

To a solution of 2.64 g (9.7 mmol) of 4,4-dimethyl-2-oxo-1,2,3,4-tetrahydro-6[(trimethylsilyl)ethynyl]quinoline (Compound 2) in 200 ml of methanol was added 0.269 g (1.95 mmol) of $K_2CO_3$ The reaction was stirred at room temperature for 12 h. The reaction was then concentrated in vacuo and water was added to the residue. The aqueous layer was extracted with methylene chloride (2×). The organic layers were dried ($MgSO_4$), filtered and concentrated in vacuo to give the title compound as a white solid.

PNMR ($CDCl_3$) d 8.29 (1H, b), 7.43 (1H, d, J=1.8 Hz), 7.32 (1H, dd, J=8.2 Hz, 1.8 Hz), 6.73 (1H, d, J=8.2 Hz), 3.05 (1H, s), 2.49 (2H, s), 1.33 (6H, s).

Ethyl 4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated $NaHCO_3$ and saturated NaCl solutions and dried ($MgSO_4$). Solvent was then removed in vacuo and the residue kugelrohr distilled (100 degrees C; 0.55 mm) to give the title compound as a colorless oil, PMR ($CDCl_3$): 1.42 (3H, t, J~7 Hz), 4,4 (2H, q, J~7 Hz), 7.8 (4H).

Ethyl 4-[4,4-dimethyl-2-oxo-1,2,3,4-tetrahydro-6-quinolinyl)ethynyl]benzoate (Compound 4)

To a solution of 1.57 g (7.9 mmol) of 4,4-dimethyl-2-oxo-1,2,3,4-tetrahydro-6-ethynylquinoline (Compound 3) and 2.31 g (8.4 mmol) of ethyl 4-iodobenzoate in 40 ml of triethylamine which was degassed under argon for 30 min, were added 0.319 g of CuI (1.7 mmol) and 1.36 g (1.94 mmol) of bis(triphenylphosphine)palladium(II) chloride. The reaction mixture was stirred at room temperature for 4 h. The reaction was then concentrated in vacuo, and the residue was purified by flash chromatography (silica, 10% ethyl acetate in hexane) to give the title compound as a solid.
PNMR ($CDCl_3$) d 8.10 (1H, b), 8.02 (2H, d, J=8.4 Hz), 7.58 (2H, d, J=8.4 Hz), 7.49 (1H, d, J=1.6 Hz), 7.38 (1H, dd, J=8.2 Hz, 1.6 Hz), 6.77 (1H, d, J=8.1 Hz) , 4.39 (q, J=7.1 Hz), 2.52 (2H, s), 1.41 (3H, t, J=7.1 Hz), 1.36 (6H, s).

Ethyl 4-[4,4-dimethyl-2-oxo-1,2,3,4-tetrahydro-1-iso-propyl-6-quinolinyl)ethynyl]benzoate (Compound 5) and Ethyl 4-[(4,4-dimethyl-2-isopropoxy-3,4-dihydro-6-quinolinyl)ethynyl]benzoate (Compound 6)

To a solution of 0.10 g (0.30 mmol) of ethyl 4-[(4,4-dimethyl-2-oxo-1,2,3,4-tetrahydro-6-quinolinyl)ethynyl]benzoate (Compound 4) in 2 ml of DMF was added 0.0155 g (0.40 mmol) of sodium hydride (prewashed with hexane), followed by 0.287 ml (3.0 mmol) of 2-iodopropane. The resulting mixture was stirred at 25° C. for 12 h under nitrogen purge. Excess solvent was removed by Kugelrohr distillation, and the residue was subjected to flash chromatography (silica gel, 10% ethyl acetate in hexane) to yield the products as white solids.

Compound 5: PNMR (5, $CDCl_3$) d 8.03 (2H, d, J=8.4 Hz), 7.60 (2H, d, J=8.4 Hz), 7.46 (1H, d, J=1.8 Hz), 7.42 (1H, dd, J=6.5 & 1.8 Hz), 7.13 (1H, d, J=8.4 Hz), 4.72 (1H, m), 4.41 (2H, q, J=7.1 Hz), 2.45 (2H, s), 1.55 (6H, d, J=7.0 Hz), 1.42 (3H, t, J=7.2 Hz), 1.32 (6H, s).

Compound 6: PNMR (6, $CDCl_3$) d 8.02 (2H, d, J=8.4 Hz), 7.59 (2H, d, J=8.4 Hz), 7.46 (1H, d, J=1.8 Hz), 7.39 (1H, dd, J=7.9 & 1.8 Hz), 7.12 (1H, d, J=7.9 Hz), 5.44 (1H, m), 4.39 (2H, q, J=7.2 Hz), 2.27 (2H, s), 1.44 (3H, t, J=7.2 Hz), 1.34 (6H, t, J=6.2 Hz), 1.28 (6H, s).

Ethyl 4-[(4,4-dimethyl-2-thio-1,2,3,4-tetrahydro-1-iso-propyl-6-quinolinyl)ethynyl]benzoate (Compound 7)

To a solution of 0.186 g (0.51 mmol) of ethyl 4-[(4,4-dimethyl-2-oxo-1,2,3,4-tetrahydro-(1-iso-propyl-6-quinolinyl)ethynyl]benzoate (Compound 5) in 5 ml of dry benzene was added 0.232 g (0.60 mmol) of Lawesson's reagent. The resulting mixture was refluxed for 3 h and filtered. The filtrate was concentrated in vacuo to an oil. Purification by flash chromatography (silica gel, 10% ethyl acetate in hexane) yielded the title compound as a yellow solid.

PNMR ($CDCl_3$) d 8.05 (2H, d, J=8.4 Hz), 7.61 (2H, d, J=8.4 Hz), 7.49 (1H, d, J=1.9 Hz), 7.44 (1H, dd, J=6.7 & 1.9 Hz), 7.35 (1H, d, J=8.5 Hz), 6.26 (1H, m), 4.41 (2H, q, J=7.1 Hz), 3.01 (2H, s), 1.54 (6H, d, J=7.1 Hz), 1.43 (3H, t, J=7.2 Hz), 1.27 (6H, s).

Ethyl 4-[(4,4-dimethyl-2-thio-1,2,3,4-tetrahydro-6quinolinyl)ethynyl]benzoate (Compound 8)

To a solution of 0.285 g (0.80 mmol) of ethyl 4-[(4,4-dimethyl-2-oxo-1,2,3,4-tetrahydro-6-quinolinyl)ethynyl] benzoate (Compound 4) in benzene (15 ml) was added 0.398 g (1.0 mmol) of Lawesson's reagent. The resulting mixture was refluxed for 3 h and filtered. The filtrate was concentrated in vacuo to an oil. Purification by flash chromatography (silica gel, 25% ethyl acetate in hexane) yielded the title compound as a yellow solid.

PNMR ($CDCl_3$) d 8.03 (2H, d, J=8.4 Hz), 7.51 (2H, d, J=8.4 Hz), 7.42 (1H, dd, J=8.2 Hz, J=1.6 Hz), 6.98 (1H, d, J=8.2 Hz), 4.41 (2H, q, J=2.9 Hz), 2.95 (2H, s), 1.41 (3H, t, J=2.9 Hz), 1.33 (6H, s).

Ethyl 4-[(4,4-dimethyl-2-methylthio-3,4-dihydro-6-quinolinyl)ethynyl]benzoate (Compound 9)

To a suspension of 0.0187 g (0.50 mmol) of NaH (washed with hexane three times) in 5 ml of THF was cannulated a solution of 0.172 g (0.50 mmol) of ethyl 4-[(4,4-dimethyl-2-thio-1,2,3,4-tetrahydro-6-quinolinyl)ethynyl]benzoate (Compound 8) in 15 ml of THF. The resulting yellow solution was stirred at room temperature for 1 h. Methyl iodide 0.295 ml (5.0 mmol) was then added dropwise and the solution stirred at room temperature for 1 h. MeOH and water were then added and the mixture was concentrated. Purification by flash chromatography (10% EtOAc in hexane) gave the title compound as an oil.

PNMR ($CDCl_3$) d 8.03 (2H, d, J=8.4 Hz), 7.59 (2H, d, J=8.5 Hz), 7.48 (1H, s), 7.44 (1H, dd, J=6.5 & 1.8 Hz), 7.26 (1H, d, J=8.0 Hz), 4.37 (2H, q, J=7.1 Hz), 2.54 (3H, s), 2.34 (2H, s), 1.40 (3H, t, J=7.1 Hz), 1.25 (6H, s).

Ethyl 4-[(4,4-dimethyl-2-heptylthio-3,4-dihydro-6-quinolinyl)ethynyl]benzoate (Compound 10)

0.025 g (0.694 mmol) of sodium hydride in 2 ml of THF, 0.229 g (0.631 mmol) of ethyl 4-[(4,4-dimethyl-2-thio-1,2,3,4-tetrahydro-6-quinolinyl)ethynyl]benzoate (Compound 8) in 2 ml of THF and 1.03 ml (6.31 mmol) of iodoheptane were reacted substantially in accordance with the procedure used for the preparation of ethyl 4-[(4,4-dimethyl-2-methylthio-3,4-dihydro-6-quinolinyl)ethynyl]benzoate (Compound 9). Purification by flash chromatography (silica gel, 10% ethyl acetate in hexane) yielded the title compound as a yellow solid.

PNMR ($CDCl_3$) d 8.04 (2H, d, J=8.4 Hz), 7.60 (2H, d, J=8.4 Hz), 7.48 (1H, d, J=1.78 Hz), 7.44 (1H, dd, J=6.2 & 1.9 Hz), 7.27 (1H, d, J=2.9 Hz), 4.42 (2H, q, J=7.1 Hz), 3.19 (2H, t, J=7.4 Hz), 2.34 (2H, s), 1.72 (2H, m), 1.61 (1H, m), 1.42 (3H, t, J=7.1 Hz), 1.33 (8H, m), 1.27 (6H, s), 0.91 (2H, m).

4-[(4,4-Dimethyl-2-iso-propoxy-3,4-dihydro-6-quinolinyl)ethynyl]benzoic acid (Compound 11)

A solution of 0.023 mg (0.06 mmol) of ethyl 4-[(4,4-dimethyl-2-iso-propoxy-3,4-dihydro-6-quinolinyl)ethynyl] benzoate (Compound 6) in 2 ml of THF, 1 ml of EtOH, and 2 ml of 1N LiOH was stirred at room temperature for 1 h. Aqueous work up yielded the title compound as a white solid.

PNMR (CD$_3$COCD$_3$) d 8.04 (2H, d, J=8.5 Hz), 7.65 (2H, d, J=8.5 Hz), 7.51 (1H, d, J=1.8 Hz), 7.39 (1H, dd, J=8.1 & 1.8 Hz), 7.10 (1H, d, J=8.1 Hz), 5.41 (1H, m), 2.30 (2H, s), 1.31 (6H, t, J=6.2 Hz), 1.27 (6H, s).

Ethyl 4-[(4,4-dimethyl-2-thio-1,2,3,4-tetrahydro-1-iso-propyl-6-quinolinyl) ethynyl]benzoic acid (Compound 12)

Employing the same procedure as for the preparation of 4-[(4,4-dimethyl-2-iso-propoxy-3,4-dihydro-6-quinolinyl)ethynyl]benzoic acid (Compound 11), but using 0.0524 g (0.129 mmol) of ethyl 4-[4,4-dimethyl-2-thio-1,2,3,4-tetrahydro-(N-isopropyl)-6-quinolinyl]ethynyl benzoate (Compound 7) in 2 ml of THF, 1 ml of EtOH, and 2 ml of 1N LiOH, the title compound was obtained as a yellow solid.

PNMR (CD$_3$OD) d 7.93 (2H, d, J=8.4 Hz), 7.52 (2H, d, J=8.4 Hz), 7.44 (1H, s), 7.39 (2H, s), 6.12 (1H, m), 2.85 (2H, s), 1.43 (6H, d, J=7.1 Hz), 1.16 (6H, s).

4-[(4,4-Dimethyl-2-thio-1,2,3,4-tetrahydro-6-quinolinyl)ethynyl]benzoic acid (Compound 13)

A solution of 0.090 mg (0.20 mmol) of ethyl 4-[(4,4-dimethyl-2-thio-1,2,3,4-tetrahydro-6-quinolinyl)ethynyl] benzoate (Compound 8) in 2 ml of THF, 1 ml of EtOH, and 2 ml of 1N LiOH was stirred at room temperature for 1 h. Aqueous work up yielded the title compound as a yellow solid.

PNMR (CD$_3$COCD$_3$) d 8.07 (2H, d, J=8.3 Hz), 7.65 (2H, d, J=8.4 Hz), 7.61 (1H, s), 7.47 (1H, dd, J=8.2 & 1.7 Hz), 7.24 (1H, d, J=8.3 Hz), 2.89 (2H, s), 1.31 (6H, s).

4-[(4,4-Dimethyl-2-methylthio-3,4-dihydro-6-quinolinyl)ethynyl]benzoic acid (Compound 14)

A solution of 0.100 g (0.30 mmol) of ethyl 4-[(4,4-dimethyl-2-methylthio-3,4-dihydro-6-quinolinyl)ethynyl] benzoate (Compound 9) in 2 ml of THF, 1 ml of EtOH and 2 ml of 1N LiOH was stirred at room temperature for 1 h, followed by aqueous work up to yield the title compound as a yellow solid.

PNMR (CD$_3$OD) d 8.01 (2H, d, J=8.4 Hz), 7.59 (2H, d, J=8.4 Hz), 7.52 (1H, d, J=1.8 Hz), 7.37 (1H, dd, J=8.2 & 1.8 Hz), 6.90 (1H, d, J=8.2 Hz), 3.29 (3H, s), 2.47 (2H, s), 1.34 (6H, s).

4-[(4,4-Dimethyl-2-heptylthio-3,4-dihydro-6-quinolinyl)ethynyl]benzoic acid (Compound 15)

0.0647 g (0.140 mmol) of ethyl 4-[(4,4-dimethyl-2-heptylthio-3,4-dihydro-6-quinolinyl)ethynyl]benzoate (Compound 10) in 2 ml of THF, 1 ml of EtOH was reacted with 2 ml of 1N LiOH substantially in accordance with the procedure used for the preparation of 4-[(4,4-dimethyl-2-iso-propoxy-3,4-dihydro-6-quinolinyl)ethynyl]benzoic acid (Compound 11). Purification by recrystallization in acetonitrile yielded the title compound as a yellow powder.

PNMR (CD$_3$OD) d 7.90 (2H, d, J=8.4 Hz), 7.47 (2H, d, J=8.4 Hz), 7.38 (1H, s), 7.29 (1H, dd, J=6.2 & 1.8 Hz), 7.09 (1H, d, J=8.0 Hz), 3.05 (2H, t, J=7.3 Hz), 2.24 (2H, s), 2.34 (2H, s), 1.60 (2H, m), 1.22 (9H, m), 1.13 (6H, s), 0.79 (3H, m).

N-3,3-Dimethylacryloyl-3-bromoaniline (Compound 17)

To a suspension of NaH (4.15 g, 173 mmol, 60% in oil) in 50 ml of THF was cannulated a solution of 20.322 g (118 mmol) of 3-bromoaniline in 50 ml of THF. The resulting mixture was stirred at 0° C. for 45 min and warmed to room temperature over a period of 15 min. To this solution was added through cannulation 13.123 g (173 mmol) of 3,3-dimethylacryloyl chloride. The mixture was stirred at room temperature for 24 h and thereafter slowly poured into ice water. The resulting mixture was extracted with methylene chloride (twice), dried over MgSO$_4$ and concentrated to yield a solid. The solid was purified by recrystallization in hexane/EtOAc (2:1) to give the title compound as a light brown solid.

PNMR (CDCl$_3$) d 7.83 (1H, b), 7.30 (4H, m), 5.68 (1H, s), 2.22 (3H, s), 1.90 (3H, s).

4,4-Dimethyl-2-oxo-1,2,3,4-tetrahydro-7-bromoquinoline (Compound 18)

Into a 500 ml round-buttom flask was placed 13.52 g (101 mmol) of AlCl$_3$ under nitrogen purge and kept at 0° C. Thereafter, 22.41 g of N-3,3-dimethylacryloyl-3-bromoaniline (Compound 17) in 350 ml CH$_2$Cl$_2$ was slowly added by syringe. The reaction mixture was stirred at 0° C. for 72 h, and thereafter slowly quenched with small chunks of ice-cubes and finally with water. The aqueous layer was washed with CH$_2$Cl$_2$ and the organic layer was dried over Na$_2$SO$_4$. The solvent was evaporated and the residue purified by recrystallization from EtOAc-hexane to give the title compound as off-white solids.

PNMR (CDCl$_3$) d 8.87 (1H, b), 7.23 (1H, d, J=7.95 Hz), 7.16 (2H, s), 7.0 (1H, s), 2.49 (2H, s), 1.32 (6H, s).

4,4-Dimethyl-2-oxo-1,2,3,4-tetrahydro-7-[(trimethylsilyl)ethynyl]quinoline (Compound 19)

2.2398 g (8.8 mmol) of 4,4-dimethyl-2-oxo-1,2,3,4-tetrahydro-7-bromoquinoline (Compound 18), 371 mg (1.9 mmol) of CuI, 1.087 g (1.5 mmol) of Pd(PPh$_3$)$_2$Cl$_2$, 35 ml (0.251 mol) of triethylamine and 4.0 ml (28.0 mmol) of trimethylacetylene were reacted substantially in accordance with the procedure used for the preparation of 4,4-dimethyl-2-oxo-1,2,3,4-tetrahydro-6-[(trimethylsilyl)ethynyl]quinoline (Compound 2) to give the title compound as pale orange solids (74%).

PNMR (CDCl$_3$) d 7.70 (1H, b), 7.23 (1H, d, J=7.95 Hz), 7.15 (1H, dd, J=7.95, 1.5 Hz), 6.84 (1H, d, J=1.5 Hz), 2.49 (2H, s), 1.32 (6H, s), 0.002 (9H, s).

4,4-Dimethyl-2-oxo-1,2,3,4-tetrahydro-7-ethynylquinoline (Compound 20)

1.77 g (6.5 mmol) of 4,4-dimethyl-2-oxo-1,2,3,4-tetrahydro-7-[(trimethylsilyl)ethynyl]quinoline (Compound 19), and 175 mg (1.3 mmol) of K$_2$CO$_3$ in 60 ml of methanol were reacted substantially in accordance with the procedure used for the preparation of 4,4-dimethyl-2-oxo-1,2,3,4-tetrahydro-6-ethynylquinoline (Compound 3), to give the title compound as an orange oil. The product was used in the next reaction without further purification.

Ethyl 4-[(4,4-dimethyl-2-oxo-1,2,3,4-tetrahydro-7-quinolinyl)ethynyl]benzoate (Compound 21)

1.29 g (6.5 mmol) of 4,4-dimethyl-2-oxo-1,2,3,4-tetrahydro-7-ethynylquinoline (Compound 20), 290 mg (1.5 mmol) of CuI, 1.14 g (1.6 mmol) of Pd(PPh$_3$)$_2$Cl$_2$, 65 ml (0.467 mol) of triethylamine and 4.25 g (15.4 mmol) of ethyl 4-iodobenzoate were reacted substantially in accordance with the procedure used for the preparation of ethyl 4-[(4,4-dimethyl-2-oxo-1,2,3,4-tetrahydro-6-quinolinyl)ethynyl]benzoate (Compound 4) to give the title compound as white solids.

PNMR (CDCl$_3$) d 8.10 (1H, b), 8.02 (2H, d, J=8.4 Hz), 7.59 (2H, d, J=8.4 Hz), 7.37 (1H, d, J=8.0 Hz), 7.23 (1H, dd, J=8.0 Hz, 1.6 Hz), 7.05 (1H, d, J=1.6 Hz), 4.37 (q, J=7.1 Hz), 2.46 (2H, s), 1.39 (3H, t, J=7.1 Hz), 1.32 (6H, s).

Ethyl 4-[(4,4-dimethyl-2-thio-1,2,3,4-tetrahydro-7-quinolinyl)ethynyl]benzoate (Compound 22)

To a suspension of (0.51 g, 1.47 mmol) of ethyl [(4,4-dimethyl-2-oxo-1,2,3,4-tetrahydro-7-quinolinyl)ethynyl]-4-benzoate (Compound 21) in 15 ml of benzene was added 0.54 g (1.3 mmol) of Lawesson's Reagent and the mixture was refluxed for 30 min. by which time TLC (30% EtOAc in hexane) indicated complete disappearance of Compound 21. The mixture was then concentrated and purified by flash chromatography (30% EtOAc in hexane) under nitrogen. The title compound crystallized from the solvent in which it had been eluted, and was collected by filtration as pale yellow crystals.

PNMR (CD$_3$OD) d 8.02 (2H, d, J=8.3 Hz), 7.60 (2H, d, J=8.5 Hz), 7.41 (1H, d, J=8.0 Hz), 7.30 (1H, dd, J=8.2 & 1.6 Hz), 7.17 (1H, d, J=1.6 Hz), 4.37 (2H, q, J=7.1 Hz), 2.86 (2H, s), 1.39 (3H, t, J=7.1 Hz), 1.27 (6H, s).

Ethyl 4-[(4,4-dimethyl-2-methylthio-3,4-dihydro-7-quinolinyl)ethynyl]benzoate (Compound 23)

To a suspension of 0.037 g (1.5 mmol) of NaH (hexane washed 3×) in 5 ml of THF was cannulated a solution of 0.24 g (0.66 mmol) of ethyl 4-[(4,4-dimethyl-2-thio-1,2,3,4-tetrahydro-7-quinolinyl)ethynyl]benzoate (Compound 22) in 15 ml of THF. The resulting yellow solution was stirred at room temperature for 1 h. Methyl iodide 0.46 g (0.20 ml, 3.2 mmol) was then added dropwise and the solution stirred at room temperature for 1 h. MeOH and water were then added and the mixture concentrated by evaporation. Purification by flash chromatography (10% EtOAc in hexane) gave the title compound as an oil.

PNMR (CDCl$_3$) d 8.02 (2H, d, J=8.3 Hz), 7.57 (2H, d, J=8.3 Hz), 7.48 (1H, d, J=1.6 Hz), 7.31 (1H, dd, J=7.9 & 1.7 Hz), 7.26 (1H, d, J=7.9 Hz), 4.39 (2H, q, J=7.1 Hz), 2.53 (3H, s), 2.34 (2H, s), 1.41 (3H, t, J=7.1 Hz), 1.24 (6H, s).

4,4-Dimethyl-2-oxo-1,2,3,4-tetrahydro-1-iso-propyl-7-bromoquinoline (Compound 24) and 4,4-Dimethyl-2-iso-propoxy-3,4-dihydro-7-bromoquinoline (Compound 25)

To a suspension of 0.034 g (14 mmol) of sodium hydride in 5.0 ml of dimethylformamide stirring at 0° C. under argon was cannulated a solution of 1.34 g (5.3 mmol) of 4,4-dimethyl-2-oxo-1,2,3,4-tetrahydro-7-bromoquinoline (Compound 18) in 10 ml of dimethylformamide. The resulting mixture was stirred while allowed to come to room temperature over a course of 2 h. 7.6 g (4.5 ml, 45 mmol) of isopropyl iodide was then added and the resulting solution stirred at room temperature for 96 h. Then the reaction mixture was cooled to 0° C., quenched with water and extracted with methylene chloride (2×). The organic layers were dried (MgSO$_4$), filtered and concentrated in vacuo. The resulting crude product was purified using flash chromatography to give the separated title compounds 24 and 25 as clear oils.

Compound 24: PNMR (24 CDCl$_3$) d 1.28 (6H, s), 1.53 (6H, d, J=6.0 Hz), 2.40(2H, s), 4.61 (1H, p, J=6.0 Hz), 7.12(1H, d, J=8.6 Hz), 7.18 (1H, dd, J=2.1 & 8.6 Hz ), 7.24 (1H, d, J=2.1 Hz ). Compound 25: PNMR (25, CDCl$_3$) d 1.23 (6H, s), 1.35 (6H, d, J=6.0 Hz), 2.22 (2H, s), 5.39 (1H, p, J=6.0 Hz), 7.12 (1H, d, J=8.4 Hz), 7.18 (1H, dd, J=1.8 & 8.4 Hz), 7.30 (1H, d, J=1.8 Hz).

4,4-Dimethyl-2-iso-propoxy-3,4-dihydro- (7-(trimethylsilyl)ethynyl)quinoline (Compound 26)

To a solution of 0.196 g (0.66 mmol) of 4,4-dimethyl-2-iso-propoxy-1,2,3,4-tetrahydro-7-bromoquinoline (Compound 25) in 3.0 ml of diethylamine which was degassed under argon for 15 min in a sealable tube, were added successively 0.049 g (0.26 mmol) of copper(I) iodide, (2.5 ml, 1.8 mmol) of (trimethylsilyl) acetylene, and 0.152 g (0.22 mmol) of bis(triphenylphosphine)palladium(II) chloride. The reaction mixture was degassed for an additional 5 min, the tube sealed and the reaction was heated at 50° C. for 96 h. The reaction mixture was then concentrated in vacuo. Purification by flash chromatography (silica, 100% hexane) gave the title compound as an oil.

PNMR (CDCl$_3$) d 0.23 (9H, s), 1.23 (6H, s), 1.54 (6H, d, J=6.3 Hz), 2.23 (2H, s), 5.40 (1H, p, J=6.3 Hz), 7.17 (2H, s), 7.33 (1H, s).

4,4-Dimethyl-2-iso-propoxy-3,4-dihydro-7-ethynylquinoline (Compound 27)

To a solution of 0.14 g (0.45 mmol) of 4,4-dimethyl-2-iso-propoxy-1,2,3,4-tetrahydro-7-[(trimethylsilyl)ethynyl] quinoline (Compound 26) in 2.5 ml of methanol was added 0.10 g (0.72 mmol) of potassium carbonate. The reaction mixture was then stirred at room temperature for 2.5 h. The reaction mixture was then concentrated in vacuo and the resulting oil was dissolved in water and extracted with methylene chloride (2×). The organic layers were dried (MgSO$_4$), filtered and concentrated in vacuo to give the title compound as an oil. This compound was used for the next reaction without further purification.

Ethyl 4-[(4,4-dimethyl-2-isopropoxy-3,4-dihydro-7-quinolinyl)ethynyl]benzoate (Compound 28)

To a solution of 0.097 g (0.40 mmol) of 4,4-dimethyl-2-isopropoxy-1,2,3,4-tetrahydro-7-ethynylquinoline (Compound 27) and 1.16 g (0.75 ml, 4.2 mmol) of ethyl 4-iodobenzoate in 3.0 ml of diethylamine which was degassed under argon for 15 min, was added 0.043 g (0.23 mmol) of copper(I) iodide and then 0.064 g (0.09 mmol) of bis(triphenylphosphine)palladium(II) chloride. The reaction was stirred at room temperature for 16 h. The reaction mixture was then concentrated. Purification by flash chromatography (1.5% EtOAc in hexane) gave the title compound as an oil. PNMR (CDCl$_3$) d 8.00 (2H, d, J=8.2 Hz), 7.54 (2H, d, J=8.1 Hz), 7.32 (1H, s), 7.23 (2H, s), 5.40 (1H, p, J=6.3 Hz), 4.37 (2H, q, J=7.1 Hz), 2.24 (2H, s), 1.39 (3H, t, J=7.1 Hz), 1.32 (6H, d, J=6.2 Hz), 1.24 (6H, s).

4,4-Dimethyl-2-oxo-1,2,3,4-tetrahydro-1-iso-propyl-7-[(trimethylsilyl)ethynyl]quinoline (Compound 29)

To a solution of 0.40 g (1.36 mmol) of 4,4-dimethyl-2-oxo-1,2,3,4-tetrahydro-1-iso-propyl-7-bromoquinoline (Compound 24) in 5.0 ml of triethylamine which was degassed under argon for 15 min in a sealable tube, were added successively 0.069 g (0.36 mmol) of copper(I)iodide, (1.0 ml, 7.1 mmol) of (trimethylsilyl)acetylene, and 0.147 g (0.21 mmol) of bis(triphenylphosphine)palladium(II) chloride. The reaction mixture was degassed for an additional 5 min. The tube was sealed and the reaction mixture was heated at 50° C. for 72 h. The reaction mixture was concentrated in vacuo. Purification by flash chromatography (silica, 10% ethyl acetate in hexane) gave the title compound as an oil. PNMR (CDCl$_3$) d 0.25 (9H, s), 1.26 (6H, s), 1.54 (6H, d, J=7.1 Hz), 2.39 (2H, s), 4.60 (1H, p, J=7.1 Hz), 7.17 (3H, m).

4,4-Dimethyl-2-oxo-1,2,3,4-tetrahydro-1-iso-propyl-7-ethynylquinoline (Compound 30)

To a solution of 4,4-dimethyl-2-oxo-1,2,3,4-tetrahydro-1-isopropyl-7-[(trimethylsilyl)ethynyl]quinoline (Compound 29) in 7.0 ml of methanol was added potassium carbonate. The mixture was stirred at room temperature for 10 h. The reaction mixture was then concentrated in vacuo and the resulting oil was dissolved in water, and extracted using methylene chloride (2×). The organic layers were dried (MgSO$_4$), filtered and concentrated in vacuo to give the title compound as an oil.

PNMR (CDCl$_3$) d 1.28 (6H, s), 1.54 (6H, d, J=7.0 Hz), 2.41(2H, s), 3.07 (1H, s), 4.65 (1H, p, J=7.0 Hz), 7.21 (3H, m).

Ethyl 4-[(4,4-dimethyl-2-oxo-1,2,3,4-tetrahydro-1-isopropyl-7-quinolinyl)ethynyl]benzoate (Compound 31)

To a solution of 0.282 g (1.17 mmol) of 4,4-dimethyl-2-oxo-1,2,3,4-tetrahydro-1-iso-propyl-7-ethynyl quinoline (Compound 30) and 0.52 g (1.9 mmol) of ethyl 4-iodobenzoate in 2.5 ml of diethylamine which was degassed under argon for 30 min, was added 0.049 g (0.26 mmol) of copper(I) iodide and then 0.159 g (0.23 mmol) of bis(triphenylphosphine)palladium(II) chloride. The reaction was stirred at room temperature for 4 h. The reaction mixture was then concentrated in vacuo. Purification by flash chromatography (silica, 10% ethyl acetate in hexane) gave the title compound as a solid.

PNMR (CDCl$_3$) d 1.30 (6H, s), 1.41 (3H, t, J=7.1 Hz), 1.59(6H, d, J=7.0 Hz), 2.44 (2H, s), 4.39 (2H, q, J=7.1 Hz), 5.32 (1H, p, J=7.0 Hz), 7.27 (3H, overlapping), 7.60 (2H, d, J=8.4 Hz), 8.04 (2H, d, J=8.4 Hz).

Ethyl 4-[(4,4-dimethyl-2-thio-1,2,3,4-tetrahydro-1-iso-propyl-7-quinolinyl)ethynyl]benzoate (Compound 32)

To a suspension of 0.168 g (0.43 mmol) of ethyl 4-[(4,4-dimethyl-2-oxo-1,2,3,4-tetrahydro-1-isopropyl-7-quinolinyl)ethynyl]benzoate (Compound 31) in 5 ml of benzene was added 0.175 g (0.43 mmol) of Lawesson's reagent and the mixture was refluxed for 24 h. The mixture was then concentrated and purified by flash chromatography (5% EtOAc in hexane) under nitrogen to give the title compound as a pale yellow solid.

PNMR (CD$_3$OD) d 8.01 (2H, d, J=8.2 Hz), 7.62 (2H, d, J=8.3 Hz), 7.52 (1H, s), 7.38 (2H, 2×d, J=8.1 Hz), 6.16 (1H, p, J=7.1 Hz), 4.36 (2H, q, J=7.1 Hz), 2.91 (2H, s), 1.53 (6H, d, J=7.1 Hz), 1.38 (3H, t, J=7.1 Hz), 1.22 (6H, s).

4- [(4,4-Dimethyl-2-thio-1,2,3,4-tetrahydro-7-quinolinyl)ethynyl]benzoic acid (Compound 33)

To a solution of 0.121 g (0.33 mmol) of ethyl 4-[(4,4-dimethyl-2-thio-1,2,3,4-tetrahydro-7-quinolinyl) ethynyl] benzoate (Compound 22) in 3.0 ml of tetrahydrofuran was added 1.0 ml (1.0 mmol) of 1.0M aqueous LiOH. The resulting solution was stirred at room temperature for 24 h. The reaction was then concentrated, water was added to the solid residue and the resulting aqueous layer was then acidified to pH=1 with 10% HCl, and extracted using diethyl ether (2×). The organic layers were dried with MgSO$_4$, filtered and concentrated to yield a residue which was washed with warm acetone to give the title compound as a solid.

PNMR (CD$_3$OD) d 8.01 (2H, d, J=8.3 Hz), 7.58 (2H, d, J=8.3 Hz), 7.38 (1H, d, J=8.0 Hz), 7.23 (1H, dd, J=7.9 & 1.6 Hz), 7.05 (1H, d, J=1.6 Hz), 2.46 (2H, s), 1.32 (6H, s).

4,4-[(4,4-Dimethyl-2-methylthio-3,4-dihydro-7-quinolinyl)ethynyl]benzoic acid (Compound 34)

To a solution of 0.068 g (0.18 mmol) of ethyl 4-[(4,4-dimethyl-2-methylthio-3,4-dihydro-7-quinolinyl)ethynyl] benzoate (Compound 23) in 3.0 ml of tetrahydrofuran was added 1.0 ml (1.2 mmol) of 1.2M aqueous LiOH. The resulting solution was stirred at room temperature for 4 h and thereafter heated at 40°–55° C. for 3 h. The reaction mixture was then concentrated and water was added to the residue. The resulting aqueous layer was acidified to pH=1 with 10% HCl, and extracted using diethyl ether(2×). The organic layers were dried (MgSO$_4$), filtered and concentrated to give the title compound as a solid.

PNMR (CDCl$_3$) d 8.09 (2H, d, J=8.4 Hz), 7.61 (2H, d, J=8.4 Hz), 7.54 (1H, s), 7.32 (2H, 2×d, J=8.6 Hz), 2.57 (3H, s), 2.37 (2H, s), 1.22 (6H, s).

4-[(4,4-Dimethyl-2-isopropoxy-3,4-dihydro-7-quinolinyl)ethynyl]benzoic acid (Compound 35)

To a solution of 0.0586 g (0.15 mmol) of 4,4-dimethyl-2-iso-propoxy-1,2,3,4-tetrahydro-7-ethynylquinoline (Compound 27) in 3.0 ml of tetrahydrofuran were added 1.0 ml (1.1 mmol) of 1.1M aqueous LiOH and 1.0 ml of methanol. The resulting solution was stirred at room temperature for 2 h. The reaction mixture was then concentrated and water was added to the residue. The aqueous layer was acidified to pH=1 with 10% HCl, and extracted with diethyl ether (2×). The organic layers were dried (MgSO$_4$), filtered and concentrated to give the title compound as a solid.

PNMR (DMSO) d 7.96 (2H, d, J=8.4 Hz), 7.65 (2H, d, J=8.4 Hz), 7.36 (1H, d, J=7.9 Hz), 7.28 (1H, dd, J=1.8 & 8.0 Hz), 7.19 (1H, d, J=1.6 Hz), 5.32 (1H, p, J=6.2 Hz), 2.29 (2H, s), 1.29 (6H, d, J=6.2 Hz), 1.19 (6H, s).

4-[4,4-Dimethyl-2-thio-1,2,3,4-tetrahydro-1-iso-propyl-7-quinolinyl)ethynyl]benzoic acid (Compound 36)

To a solution of 0.115 g (0.28 mmol) of ethyl 4-[(4,4-dimethyl-2-thio-1,2,3,4-tetrahydro-1-iso-propyl-7-quinolinyl)ethynyl]benzoate (Compound 32) in 7.0 ml of tetrahydrofuran was added 1.0 ml (1.2 mmol) of 1.2M aqueous LiOH. The resulting solution was stirred at room temperature for 48 h. The reaction mixture was concentrated and water was added to the residue, and the aqueous solution was washed with hexane. The aqueous layer was acidified to pH=1 with 10% HCl, and extracted with (3:1) diethyl ether/methylene chloride (2×). The organic layers were dried (Na$_2$SO$_4$), filtered and concentrated to yield the title compound as a solid.

PNMR (CDCl$_3$) d 7.96 (2H, d, J=8.4 Hz), 7.65 (2H, d, J=8.4 Hz), 7.36 (1H, d, J=7.9 Hz), 7.28 (1H, dd, J=1.8 & 8.0 Hz), 7.19 (1H, d, J=1.6 Hz), 5.32 (1H, p, J=6.2 Hz), 2.29 (2H, s), 1.29 (6H, d, J=6.2 Hz), 1.19 (6H, s).

Ethyl 4- [(4,4-dimethyl-2-oxo-1,2,3,4-tetrahydro-1-benzyl-6-quinolinyl)ethynyl]benzoate (Compound 37)

NaH (93.6 mg, 2.6 mmol), ethyl 4-(4,4-dimethyl-2-oxo-1,2,3,4-tetrahydro-6-quinolinyl) ethynyl benzoate (Compound 4, 604 mg, 1.7 mmol) and benzyl bromide (2.06 mL, 17 mmol) in 3 mL of DMF were reacted substantially in accordance with the procedure used for the preparation of ethyl 4-[(4,4-dimethyl-2-oxo-1,2,3,4-tetrahydro-(1-iso-propyl-6-quinolinyl)ethynyl]benzoate (Compound 5), to yield the title compound as white solids (744 mg).

$^1$H NMR δ8.02 (d, J=8.5 Hz, 1H), 7.57 (d, J=8.5 Hz, 1H), 7.49 (d, J=1.9 Hz, 1H), 7.3 (m, 6H), 6.90 (d, J=8.5 Hz, 1H), 5.23 (s, 2H), 4.38 (q, J=7.2 Hz, 2H), 2.68 (s, 2H), 1.41 (t, J=7.2 Hz, 3H), 1.37 (s, 6H).

Ethyl 4-[(4,4-dimethyl-2-oxo-1,2,3,4-tetrahydro-1-heptyl-6-quinolinyl)ethynyl]benzoate (Compound 38)

NaH (98.4 mg, 2.7 mmol), ethyl 4-[(4,4-dimethyl-2-oxo-1,2,3,4-tetrahydro-6-quinolinyl )ethynyl]benzoate (Compound 4, 635 mg, 1.8 mmol) and iodo heptane (2.73 mL, 18 mmol) in 3 mL of DMF were reacted substantially in accordance with the procedure used for the preparation of ethyl 4-[(4,4-dimethyl-2-oxo-1,2,3,4-tetrahydro-1-iso-propyl-6-quinolinyl)ethynyl]benzoate (Compound 5), to give the title compound as white solids.

$^1$H NMR δ8.04 (d, J=8.3 Hz, 1H), 7.60 (d, J=8.5 Hz, 1H), 7.49 (d, J=1.9 Hz, 1H), 7.43 (dd, J$_1$=1.9 Hz, J$_2$=8.3 Hz, 1H), 7.00 (d, J=8.5 Hz, 1H), 4.39 (q, J=7.2 Hz, 2H), 3.97 (t, J=7.9 Hz, 2H), 2.52 (s, 2H), 1.6 (m, 2H), 1.41 (t, J=7.2 Hz, 3H), 1.35 (m, 10H), 1.32 (s, 6H), 0.89 (t, J=6.7 Hz, 3H).

4-[(4,4-Dimethyl-2-oxo-1,2,3,4-tetrahydro-1-benzyl-6-quinolinyl)ethynyl]benzoic acid (Compound 39)

95.6 mg (0.23 mmol) of ethyl 4-[(4,4-dimethyl-2-oxo-1,2,3,4-tetrahydro-1-benzyl-6-quinolinyl)ethynyl]benzoate (Compound 37) in 2 ml of THF, 2 ml of EtOH, and 1 ml of 1N LiOH were reacted substantially in accordance with the procedure used for the preparation of 4-[4,4-dimethyl-2-isopropoxy-1,2,3,4-tetrahydro-6-quinolinyl]ethynyl benzoic acid (Compound 11) to give the title compound as a white solid (131 mg).

$^1$H NMR δ8.09 (d, J=8.5 Hz, 1H), 7.60 (d, J=8.5 Hz, 1H), 7.30 (m, 6H), 6.91 (d, J=8.5 Hz, 1H), 5.24 (s, 2H), 2.69 ( s, 2H), 1.38 ( s, 6H).

4-[4,4-Dimethyl-2-oxo-1,2,3,4-tetrahydro-1-heptyl-6-quinolinyl)ethynyl]benzoic acid (Compound 40)

163 mg (0.39 mmol) of ethyl 4-[(4,4-dimethyl-2-oxo-1,2,3,4-tetrahydro-1-benzyl-6-quinolinyl)ethynyl]benzoate (Compound 37) in 2 ml of THF, 2 ml of EtOH, and 2 ml of 1N LiOH were reacted substantially in accordance with the procedure used for the preparation of 4-[(4,4-dimethyl-2-iso-propoxy-3,4-dihydro-6-quinolinyl)ethynyl]benzoic acid (Compound 11) to give the title compound as a white flaky solid.

$^1$H NMR δ 8.11 (d, J=8.3 Hz, 1H), 7.61 (d, J=8.5 Hz, 1H), 7.49 (d, J=1.9 Hz, 1H), 7.44 (dd, J$_1$=1.9 Hz, J$_2$=8.3 Hz, 1H), 7.01 (d, J=8.5 Hz, 1H), 3.98 (t, J=7.9 Hz, 2H), 2.55 (s, 2H), 1.66 (m, 2H), 1.32 (m, 16H), 0.89 (t, J=6.7 Hz, 3H).

What is claimed is:

1. A compound of the formula

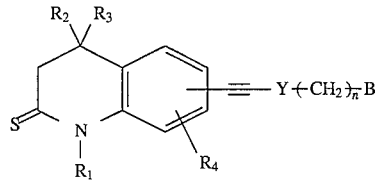

wherein R$_1$ is lower alkyl of 1 to 10 carbons or benzyl;

R$_2$ and R$_3$ are hydrogen, lower alkyl of 1–6 carbons, or halogen;

R$_4$ is hydrogen, lower alkyl of 1–6 carbons, halogen, OR$_{11}$, SR$_{11}$, OCOR$_{11}$, SCOR$_{11}$, NH$_2$, NHR$_{11}$, N(R$_{11}$)$_2$, NHCOR$_{11}$ or NR$_{11}$COR$_{11}$;

Y is phenyl or a heteroaryl group selected from a group consisting of pyridyl, thienyl, furyl, pyridazinyl, pyrimidinyl, pyrazinyl, thiazolyl, imidazolyl and oxazolyl;

n is 0–5, and B is COOH or a pharmaceutically acceptable salt thereof, COOR$_8$, or CONR$_9$R$_{10}$ where R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl.

2. A compound of the formula

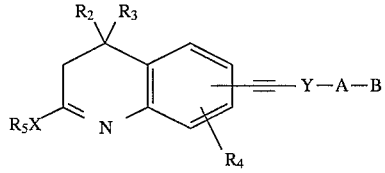

wherein X is O;

R$_5$ is lower alkyl of 1 to 10 carbons, lower alkenyl of 2 to 10 carbons, phenyl C$_1$–C$_6$ lower alkyl, phenyl C$_2$–C$_6$ lower alkenyl, heteroaryl C$_1$–C$_6$ lower alkyl, heteroaryl C$_2$–C$_6$ lower alkenyl;

R$_2$ and R$_3$ are hydrogen, lower alkyl of 1–6 carbons, or halogen;

R$_4$ is hydrogen, lower alkyl of 1–6 carbons, halogen, OR$_{11}$, SR$_{11}$, OCOR$_{11}$, SCOR$_{11}$, NH$_2$, NHR$_{11}$, N(R$_{11}$)$_2$, NHCOR$_{11}$ or NR$_{11}$COR$_{11}$;

Y is phenyl or a heteroaryl group selected from a group consisting of pyridyl, thienyl, furyl, pyridazinyl, pyrimidinyl, pyrazinyl, thiazolyl, imidazolyl and oxazolyl;

A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

3. A compound in accordance with claim 2 wherein R$_5$ is lower alkyl or benzyl.

4. A compound in accordance with claim 3 wherein A is (CH$_2$)$_n$, and B is COOH or a pharmaceutically acceptable salt thereof, COOR$_8$, or CONR$_9$R$_{10}$.

5. A compound in accordance with claim 2 wherein X is S.

6. A compound in accordance with claim 5 wherein R$_5$ is lower alkyl or benzyl.

7. A compound in accordance with claim 6 wherein A is (CH$_2$)$_n$, and B is COOH or a pharmaceutically acceptable salt thereof, COOR$_8$, or CONR$_9$R$_{10}$.

8. A compound of the formula

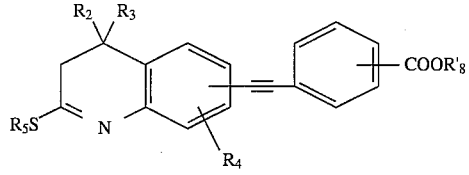

where R$_5$ is lower alkyl of 1 to 10 carbons, or phenyl C$_1$–C$_6$ lower alkyl;

R$_2$ and R$_3$ are hydrogen, or lower alkyl of 1–6 carbons;

R$_4$ is hydrogen, lower alkyl of 1–6 carbons, or halogen, and R'$_8$ is H, an alkyl group of 1 to 10 carbons, or a cycloalkyl group of 5 to 10 carbons, or R$_8$ is phenyl or lower alkylphenyl.

9. A compound in accordance with claim 8 wherein R$_5$ is lower alkyl of 1 to 10 carbons, or benzyl.

10. A compound in accordance with claim 9 wherein R$_2$ and R$_3$ are methyl and R$_4$ is H.

11. A compound in accordance with claim 10 wherein R'$_8$ is H, or lower alkyl of 1 to 6 carbons.

12. A compound in accordance with claim 11 wherein the phenyl group is 1,4 (para) substituted.

13. A compound in accordance with claim 12 which is:

(1) ethyl 4-[(4,4-dimethyl-2-methylthio-3,4-dihydro-6-quinolinyl)ethynyl]benzoate;

(2) ethyl 4-[(4,4-dimethyl-2-heptylthio-3,4-dihydro-6-quinolinyl)ethynyl]benzoate;

(3) 4-(4,4-dimethyl-2-methylthio-3,4-dihydro-6-quinolinyl)ethynyl]benzoic acid;

(4) 4-[(4,4-dimethyl-2-heptylthio-3,4-dihydro-6-quinolinyl)ethynyl]benzoic acid;

(5) ethyl 4-[(4,4-dimethyl-2-methylthio-3,4-dihydro-7-quinolinyl)ethynyl]benzoate, and (6) 4-[(4,4-dimethyl-2-methylthio-3,4-dihydro-7-quinolinyl)ethynyl]benzoic acid.

14. A compound of the formula

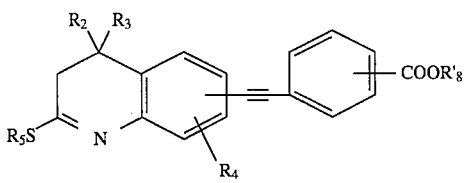

where $R_5$ is lower alkyl of 1 to 10 carbons, or phenyl $C_1$–$C_6$ lower alkyl;

$R_2$ and $R_3$ are hydrogen, or lower alkyl of 1–6 carbons;

$R_4$ is hydrogen, lower alkyl of 1–6 carbons, or halogen, and $R'_8$ is H, an alkyl group of 1 to 10 carbons, or a cycloalkyl group of 5 to 10 carbons, or $R_8$ is phenyl or lower alkylphenyl.

15. A compound in accordance with claim 14 wherein $R_5$ is H, lower alkyl of 1 to 10 carbons, or benzyl.

16. A compound in accordance with claim 15 wherein $R_2$ and $R_3$ are methyl and $R_4$ is H.

17. A compound in accordance with claim 16 wherein $R'_8$ is H, or lower alkyl of 1 to 6 carbons.

18. A compound in accordance with claim 17 wherein the phenyl group is 1,4 (para) substituted.

19. A compound in accordance with claim 18 which is:
(1) ethyl 4-[(4,4-dimethyl-2-iso-propoxy-3,4-dihydro-6-quinolinyl)ethynyl]benzoate;
(2) 4-[(4,4-dimethyl-2-iso-propyloxy-3,4-dihydro-6-quinolinyl)ethynyl]benzoic acid;
(3) ethyl 4-[(4,4-dimethyl-2-iso-propyloxy-3,4-dihydro-7-quinolinyl)ethynyl]benzoate, and
(4) 4-[(4,4-dimethyl-2-iso-propyloxy-3,4-dihydro-7-quinolinyl)ethynyl]benzoic acid.

* * * * *

UNITED STATES PATENT AND TRADEMARK OFFICE
CERTIFICATE OF CORRECTION

PATENT NO. : 5,616,712

DATED : April 1, 1997

INVENTOR(S) : Teng et al.

Page 1 of 3

It is certified that error appears in the above-indentified patent and that said Letters Patent is hereby corrected as shown below:

On the title page: Item [54], "TETRAHDROQUINOLINYL" should be --TETRAHYDROQUINOLINYL--.

Column 1, line 3, "TETRAHDROQUINOLINYL" should be --TETRAHYDROQUINOLINYL--.

Column 6, line 14, "COOR$_8$'" should be --COOR'$_8$--.

Column 6, line 18, "R$_1$'" should be --R'$_1$--.

Column 6, line 24, "R$_1$'X'" should be --R'$_1$X'--.

Column 7, line 26, after "increases", delete ".".

Column 8, line 13, "EMBODIMENT" should be --EMBODIMENTS--.

Column 11, line 20, "Dea" should be --DEA--.

Column 11, line 57, "Dea" should be --DEA--.

Column 12, line 29, after "Patent", delete "No.".

Column 13, line 57, delete "U.S. Pat. No.".

Column 15, line 42, after "4-[", add --(--.

Column 16, line 14, after "-6", add -- - --.

Column 17, line 20, "quinoliny-" should be --quinolinyl- --.

Column 18, line 22, "[(trimethy-" should be --[(trimethyl- --.

Column 21, line 42, "4,4-[(4,4-" should be --4-[(4,4- --.

Column 23, line 39, after "carbons,", add --or R$_8$ is phenyl or lower alkylphenyl, R$_9$ and R$_{10}$ independently are hydrogen, an alkyl group of 1-10 carbons, or a cycloalkyl group of 5-10 carbons,--.

UNITED STATES PATENT AND TRADEMARK OFFICE
CERTIFICATE OF CORRECTION

PATENT NO. : 5,616,712
DATED : April 1, 1997
INVENTOR(S) : Teng et al.

Page 2 of 3

It is certified that error appears in the above-indentified patent and that said Letters Patent is hereby corrected as shown below:

Column 1, line 64, the first occurrence of "disubsituted" should be --disubstituted--.
Column 1, line 64, the second occurrence of "disubsituted" should be --disubstituted--.
Column 1, line 65, "disubsituted" should be --disubstituted--.
Column 4, line 63, "adddition" should be --addition--.
Column 6, line 66, "it" should be --its--.
Column 7, line 16, "disease" should be --diseases--.
Column 7, line 38, "expresed" should be --expressed--.
Column 12, line 45, "(trimethylsily)acetylene" should be --(trimethylsilyl)acetylene--.
Column 12, line 58, "substitutent" should be --substituent--.
Column 13, line 3, "subsituent" should be --substituent--.
Column 14, line 31, "dimethlaminopyridine" should be --dimethylaminopyridine--.
Column 15, line 6, after "$K_2CO_3$", add --.--.
Column 15, line 25, "4,4" should be --4.4--.
Column 18, line 9, "round-buttom" should be --round-bottom--.
Column 22, line 7, after "4-[", add --(--.
Column 22, line 66, after "4-[", add --(--.

UNITED STATES PATENT AND TRADEMARK OFFICE
CERTIFICATE OF CORRECTION

PATENT NO. : 5,616,712  
DATED : April 1, 1997  
INVENTOR(S) : Teng et al.

Page 3 of 3

It is certified that error appears in the above-indentified patent and that said Letters Patent is hereby corrected as shown below:

Column 24, line 23, "5." should be --$SR_5$--.

Signed and Sealed this

Eighteenth Day of August, 1998

Attest:

BRUCE LEHMAN

Attesting Officer  Commissioner of Patents and Trademarks